US005690913A

United States Patent [19]

Hsu et al.

[11] Patent Number: 5,690,913
[45] Date of Patent: Nov. 25, 1997

[54] MULTILAYER BICARBONATE/PEROXIDE DENTIFRICE

[75] Inventors: Donald P. Hsu, Monmouth Junction; Rajnish Kohli, Belle Meade; Richard J. Crawford, Asbury; Nagarj S. Dixit, Plainsboro; Michael A. Collins, Hazlet; David B. Viscio, Monmouth Junction, all of N.J.

[73] Assignee: Colgate Palmolive Company, New York, N.Y.

[21] Appl. No.: 688,322

[22] Filed: Jul. 30, 1996

Related U.S. Application Data

[62] Division of Ser. No. 339,370, Nov. 14, 1994, Pat. No. 5,599,525.

[51] Int. Cl.$^6$ .................. A61K 7/16; A61K 7/20; A61K 33/40

[52] U.S. Cl. .................. 424/53; 424/49; 424/613; 424/717

[58] Field of Search .................. 424/49–58

[56] References Cited

U.S. PATENT DOCUMENTS

| | | | |
|---|---|---|---|
| 4,098,435 | 7/1978 | Weyn | 222/94 |
| 4,211,341 | 7/1980 | Weyn | 222/94 |
| 4,487,757 | 12/1984 | Kiozpeoplov | 424/49 |
| 4,687,663 | 8/1987 | Schaeffer | 222/96 |
| 5,020,694 | 6/1991 | Pettengill et al. | 222/137 |
| 5,038,963 | 8/1991 | Pettengill et al. | 222/145 |
| 5,324,505 | 6/1994 | Kornettka et al. | 424/49 |
| 5,565,190 | 10/1996 | Santalucia et al. | 424/53 |
| 5,599,525 | 2/1997 | Hsu et al. | 424/49 |
| 5,599,527 | 2/1997 | Hsu et al. | 424/52 |
| 5,614,174 | 3/1997 | Hsu et al. | 424/49 |
| 5,616,313 | 4/1997 | Williams et al. | 424/49 |
| 5,632,972 | 5/1997 | Williams et al. | 424/49 |

FOREIGN PATENT DOCUMENTS

| | | |
|---|---|---|
| 2162536 | 5/1996 | Canada . |
| 2162821 | 5/1996 | Canada . |
| 2162885 | 5/1996 | Canada . |
| 712624 | 5/1996 | European Pat. Off. . |
| 9426606 | 11/1994 | WIPO . |

*Primary Examiner*—Shep K. Rose
*Attorney, Agent, or Firm*—Paul Shapiro

[57] ABSTRACT

An extrudable composite multilayer dentifrice composition for cleaning teeth containing reactive bicarbonate and peroxide ingredients which do not interact during storage or when extruded together from a container onto a toothbrush but react in the oral cavity when mixed during tooth brushing, the composition comprising two separate dentifrice components, one component containing a peroxide ingredient and the other component containing a colorant reactive with the peroxide ingredient, the components having substantially equivalent viscosity which are maintained in stable discrete layered phases in interfacial contact with each other prior to extrusion without interaction of the peroxide and the colorant and which are extrudable together in interfacial contact without interaction of the ingredients.

4 Claims, No Drawings

MULTILAYER BICARBONATE/PEROXIDE DENTIFRICE

This is a Division of application Ser. No. 08/339,370 filed Nov. 14, 1994, now U.S. Pat. No. 5,599,525, issued Feb. 4, 1997.

BACKGROUND OF THE INVENTION

1. Field of the Invention

The invention relates generally to a multilayer dentifrice composition containing reactive ingredients and more particularly to a striped toothpaste of improved storage stability containing reactive peroxide and bicarbonate ingredients.

2. The Prior Art

Aesthetic effects have been acknowledged to play an important role in consumer acceptance of many products. In many cases ornamental effects have been used to distinguish particular products in the market place and identify products having particular distinct properties. In the dentifrice field, toothpastes and gels having contrasting stripes are known. Such stripes provide an aesthetic effect which the user finds pleasing and promotes the use of the dentifrice, particularly by children. Although such products have met with consumer approval, it has been found difficult to formulate striped dentifrice products when the ingredients in the toothpaste composition are reactive as in the case of dentifrice compositions containing peroxide compounds. For example, it has been found to be very desirable to incorporate peroxide compounds in dentifrice compositions, the efficacy of peroxide compounds in oral hygiene having long been recognized. Such compounds have been proven effective in the treatment of gingivitis, periodontitis and in combating plaque. Additionally, peroxide compounds have been utilized for oral cosmetic purposes such as tooth whitening which results from bleaching and cleansing of tooth surfaces. A problem encountered with dentifrices formulated with peroxide compounds, is that the peroxides tend to bleach the dyes incorporated in the dentifrice for striping effect causing undesirable fading and discoloration of the stripe.

In addition to the color fading problem, when peroxide compounds are utilized in combination with conventionally employed constituent ingredients of dentifrices such as alkaline abrasive agents such as sodium bicarbonate, the tendency of the peroxide compounds to react with such other ingredients presents significant problems and difficulties are encountered with respect to providing products which achieve adequate shelf life.

Examples of prior art attempts at providing stable peroxide containing dentifrices in which a bicarbonate ingredient is also included are found in the disclosures of U.S. Pat. No. 4,971,782, U.S. Pat. No. 4,897,258 and U.S. Pat. No. 4,837,008.

U.S. Pat. No. 4,837,008 discloses an aqueous dentifrice containing a peroxide and/or bicarbonate ingredient in which the ingredients are provided with a barrier coating to prevent reaction of the ingredients. A disadvantage to such dentifrice is that release of the ingredients for cleaning effect during use is diminished by the presence of the barrier coating.

U.S. Pat. No. 4,897,258 discloses an anhydrous dentifrice containing calcium peroxide and sodium bicarbonate wherein the anhydrous state of the dentifrice prevents reaction between the ingredients. A disadvantage to such dentifrice is that in spite of the anhydrous state of the dentifrice, limited storage stability is experienced.

U.S. Pat. No. 4,971,782 discloses an anhydrous dentifrice containing peroxide and bicarbonate ingredients in which one of the ingredients is coated with a water dissolvable coating and a peroxide stabilizer is included in the dentifrice to further enhance storage stability. In spite of the presence of the stabilizer, the dentifrice remains deficient in storage stability required for commercial use.

Because of the storage stability problems with dentifrices containing reactive ingredients such as peroxides and bicarbonate compounds, dentifrices containing either the peroxide or bicarbonate compound are separately maintained before use. For example, U.S. Pat. No. 4,687,663 discloses placing each of a peroxide gel and bicarbonate paste into separate compartments of a single two-compartment container to avoid interaction between these ingredients before use. Such dual packaging devices are costly to manufacture and attempts at simultaneous even delivery of the two separate dentifrice components from the dual compartmented device is many times erratic.

There is therefore a need in the art for a dentifrice containing peroxide and other reactive ingredients such as bicarbonate salts which dentifrice remains stable during storage for extended periods of time and can be stored without provision for costly physical separation of components.

SUMMARY OF THE INVENTION

In accordance with the present invention there is provided a multilayer two component dentifrice product in which the components are arranged in opposed parallel layers in interfacial contact when placed in a container, the layers being differentiated from one another by product composition, wherein each layer contains an ingredient which is reactive with an ingredient in the other layer, the layers being substantially equivalent rheologically to preclude diffusion of ingredients through the interfacial boundry. The ingredients contained in the components when mixed together are reactive with each other in the aqueous environment of the oral cavity but remain substantially unreactive while stored in the container and upon simultaneous extrusion therefrom.

When the components of the multilayer dentifrice of the present invention contain different or contrasting colorants, the dentifrice produced by the simultaneous extrusion of these components is a unitary, form retaining, striped product of sufficient thickness to rest atop normal toothbrush bristles without discending between them. During storage the multilayer two component dentifrice shows little or no tendency for any of the ingredients to leach, bleed or otherwise diffuse from one layer to another. The absence of reactivity between ingredients of the multilayer product, inspire of prolonged interfacial contact, allows the component layers to be stored together without provision for any physical separation means, thereby permitting the use of tubes and other devices conventionally used for the packaging of toothpastes, gels and other extrudable semi-solid dentifrice products.

DESCRIPTION OF THE PREFERRED EMBODIMENTS

Each vehicle used to prepare the individual layers of the multilayer, two component dentifrice of the present invention is substantially identical in composition so as to obtain a substantial rheological equivalence between the layers and to prevent diffusion or other migration of ingredients across the interfacial boundry surfaces of the abutting layers. By the term "substantially equivalent rheologies" or "substantial rheological equivalence" is meant that the two components of the multilayer two component dentifrice of the present invention have sufficiently similar viscosities so that diffusion and/or mixing of the ingredients and premature reaction of the ingredients is avoided between the layers during storage until dispensed and mixed in the oral cavity.

Expressed on a numerical basis, the viscosities of each of the dentifrice components based on the Brookfield system range from about 10 to about $80 \times 10^6$ centipoise per second (cps) at 23° C. and preferably about 15 to about $60 \times 10^6$ cps. At a viscosity above about $80 \times 10^6$ cps the viscosity of the dentifrice components is too high to meet the flow requirements of commercial filling operations. At a viscosity below about $10 \times 10^6$ cps, the fluidity of the dentifrice components creates miscibility problems between the components during commercial filling operations. The viscosity expressed as cps is measured with a Brookfield Digital Viscometer Model DVII using spindle number 95 at 5 revolutions per minute at 23° C. Within the preferred viscosity range, the viscosity of each of the dentifrice components is sufficiently similar so that during storage the components behave like a single layer and stay in position when joistled during handling or shipping.

The vehicle used to prepare the multilayer dentifrice composition of the present invention is substantially anhydrous and includes a suitable humectant which is a substantially anhydrous viscous material, such as glycerin, propylene glycol, polyethylene glycol, or any suitable mixture thereof. A mixture of glycerin and a polyethylene glycol is preferred as the humectant in the practice of the present invention. Limited amounts of water may be included in the vehicle of the dentifrice components and preferably no more than about 9% by weight of the composition. When water is present in the dentifrice components in amounts in excess of about 9% by weight, the stability of the dentifrice components begins to be adversely affected.

The amount of vehicle used in the practice of the invention is preferably sufficient to impart to the mixture the pasty consistency, body and non-tacky nature which is characteristic of conventional dental creams or gels. As is well known, such pastes and gels are extrudable from ordinary collapsible toothpaste tubes to form a ribbon of substantial thickness, e.g., about 0.5 to 1 cm. which if left undisturbed, substantially retains its original thickness over a period of one minute or more and does not penetrate substantially into the bristles of a toothbrush when resting on the ends of such bristles for a similar period. This form retention property of the multilayer dentifrice composition of the present invention is helpful in preventing mixing and premature reaction between the extruded toothpaste components before commencement of tooth brushing.

The proportion of vehicle in each of the dentifrice components of the present invention is generally within the range of about 40 to about 70% by weight of of the paste or gel dentifrice component of this invention and preferably about 50 to about 65% by weight of the dentifrice component. Glycerin is present in the dentifrice vehicle of the present invention at a concentration of about 10 to about 60% by weight and preferably about 15 to about 40% by weight.

A surfactant is used in the preparation of dentifrice composition of the present invention to aid in the thorough dispersion of the dentifrice composition throughout the oral cavity when applied thereto as well as to improve the cosmetic acceptability and detersive and foaming properties of the dentifrice. Among the organic surfactants useful in the practice of the present invention are salts of the higher alkyl sulfates, such as sodium lauryl sulfate (SLS) or other suitable alkyl sulfate having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of a fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isothionic acid or with glycerol monosulfate, such as the sodium salt of monosulfated monoglyceride of hydrogenated coconut oil fatty acids; salts of olefin sulfontates, e.g. alkene sulfonates or hydroxylakene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium (which is preferred), potassium or mono-, di or triethanol amine.

The surfactant is included in the dentifrice vehicle of the present invention at a concentration of about 0.5 to about 3.0% by weight and preferably about 1.0 to about 2.0% by weight.

Polishing agents are incorporated in both dentifrice components of the present invention and preferred polishing agents are siliceous materials, such as silica, and will normally have a mean particle size up to about 10 microns and a very high surface area, e.g. in the range of 150–750 square meters/gram. A preferred silica is a precipitated amorphous hydrated silica, such as Sorbosit AC-35 marketed by Crosfield Chemicals, or Zeodent 115 from J.M. Huber Company but other polishing agents may also be employed, including sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, aluminum silicate, zirconium silicate, calcined alumina and bentonite.

The polishing agent is present in the dentifrice composition of the present invention at a concentration of about 10 to about 30% by weight and preferably 15 to about 25% by weight.

Inorganic thickeners may be included in the dentifrices of the present invention and include fumed silicas such as Cabosil available from Cabot Corporation, and thickening silicas including those available from W.R. Grace designated Sylox 15.

Organic thickeners such as natural and synthetic gums and colloids may also be incorporated in the dentifrice composition of the present invention, particularly when water in amounts up to about 9% by weight are present in the dentifrice component. Examples of such thickeners include carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The inorganic or organic thickener may be incorporated in the compositions of the present invention at a concentration of about 0.05 to about 2% by weight and preferably about 0.1 to about 1.5% by weight.

The peroxide compound used as an ingredient in a dentifrice component of the present invention, is present in the dentifrice composition at a concentration of about 0.25 to about 5% by weight and preferably about 0.5 to about 2.0% by weight. Peroxide compounds suitable for use in the practice of the present invention include metal peroxides such as calcium peroxide, magnesium peroxide, and zinc peroxide.

When 0–9% by weight water is present in the vehicle composition used to prepare the dentifrice components of the present invention, it has been found desirable to include in the individual dentifrice components a water soluble alkali metal compound which functions to inhibit the formation of undesirable gaseous products during storage. Examples of such alkali metal compounds include alkali metal hydroxides, carbonates, sesquicarbonates, borates and silicates specific examples of which are sodium hydroxide, potassium hydroxide, sodium carbonate, potassium carbonate, sodium borate, sodium sesquicarbonate and sodium silicate.

The water soluble alkali metal compounds are incorporated in the compositions of the present invention at concentratons in the range of about 1.0 to about 4.0% by weight and preferably about 2.0 to about 3.0% by weight.

Bicarbonate compounds are included the dentifrice components of the present invention at a concentration of about 5 to about 20% by weight and preferably about 8 to about 15% by weight. The particle size of the bicarbonate compound can range from about 10 to about 300 microns although a particle size of 20–60 microns is preferred, the smaller particle size bicarbonate being more readily dispersed in the anhydrous vehicle.

Fluoride-providing salts having anti-caries efficacy may also be incorporated in the dentifrice of the present invention and are characterized by their ability to release fluoride ions in water. It is preferable to employ a water-soluble salt fluoride providing about 10–2,000 ppm of fluoride ion, and preferably about 1000–1500 ppm of fluoride ion. Among these materials are water-soluble inorganic metal salts, for example, sodium fluoride, potassium fluoride, sodium monofluorophosphate and sodium fluorosilicate. Sodium fluoride and sodium monofluorophosphate are preferred fluoride-providing salts.

Salts having anti-tartar efficacy including water soluble salts such as dialkali or tetra-alkali metal pyrophosphate salts such as $Na_4P_2O_7$ (TSPP) $K_4P_2O_7$, $Na_2K_2P_2O_7$, $Na_2H_2P_2O_7$ and $K_2H_2P_2O_7$, long chain polyphosphate such as sodium hexametaphosphate and cyclic phosphates such as sodium trimetaphosphate as well as alkali metal tripolyphosphates such as sodium tripolyphosphate (STPP) and potassium tripolyphosphate may be incorporated in the dentifrice products of the present invention preferably at a concentration of about 0.5 to about 8.0% by weight.

A striped dentifrice product is obtained in accordance with the practice of the present invention wherein colorants of contrasting colors are incorporated in each of the dentifrice components used in the practice of the present invention, the colorants being pharmacologoically and physiologically non-toxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a particle size in the range of 5–1000 microns, preferably 250–500 microns, and are present at a concentration of 0.5 to 3% by weight.

The dyes used in the practice of the present invention are distributed uniformly throughout the dentfrice component and are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4- hydroxy-2-sulfoniumphenyl)-methylene}-[1-(N-ethyI-N-p-sulfobenzyl)-A-3,5-cyclohexadienimine], FD&C Blue No. 1 (disodium salt of dibenzyldiethyldiaminotriphenylcarbinol trisulfonic acid anhydrite), FD&C Blue No. 2(sodium salt of disulfonic acid of indigotin) and mixtures thereof in various proportions. The concentration of the dye for the most effective result in the present invention is present in the dentifrice composition in an amount from about 0.0005 percent to about 2 percent by weight.

It is preferred that the colorant included in one of the dentifrice components be a pigment such as $TiO_2$ and that colorant distributed throughout the body of the other dentifrice component be a dye and the dye be of a different color than the colorant included in the first dentifrice component. To avoid bleaching of the dye by the peroxide ingredient of the dentifrice component, it is critical that the peroxide ingredient not be included in the dentifrice component layer in which a peroxide sensitive dye ingredient is included. Because the dentifrice components are substantially rheologically equivalent, migration or diffusion of peroxide compound from one dentifrice component to another through the interfacial boundry between the abutting layers is substantially reduced with the result that color fading of the dye is avoided.

Any suitable flavoring or sweetening material may also be employed. Examples of suitable flavoring constituents are flavoring oils, e.g., oils of spearmint, pepermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Various other materials may be incorporated into the dentifrice components of this invention. Non-limiting examples thereof include preservatives, silicones and chlorophyll compounds, antibacterial agents such as chlorohexidene, halogenated diphenyl ethers such as Triclosan, desensitizing agents such as potassium nitrate and potassium citrate and mixtures thereof. These adjuvants are incorporated in the dentifrice components in amounts which do not substantially adversely affect the properties and characteristics desired, and are selected and used in proper amounts, depending upon the particular type of dentifrice component involved.

To prepare the peroxide dentifrice component of the present invention, the humectants e.g. glycerin, polyethylene glycol ingredients and sweetner are dispersed in a conventional mixer until the mixture becomes a homogeneous gel phase. Into the gel phase are added a pigment such as $TiO_2$ and any tartar control agents such as TSPP or STPP or both and fluoride anti-caries agents such as sodium monofluorophosphate. These ingredients are mixed until a homogeneous phase is obtained. Thereafter the thickener, polishing agent, sodium bicarbonate, peroxide, flavor and surfactant ingredients are added and the ingredients mixed at high speed under vacuum of about 20–100 mm Hg. The resultant product is a homogeneous, semi-solid, extrudable paste product.

To prepare the second, dye containing component, the procedure identical to that described above is employed except that dye ingredients are incorporated in the initial mixture of humectants and sweetner and $TiO_2$ and the peroxide compound are omitted from the dentifrice component formulation.

The multilayer layer dentifrice composition of the present invention, is packaged in a suitable dispensing container such as a compressible dentifrice tube or mechanically operated or pressure differential dispenser wherein separate dentifrice components of substantially equivalent rheologies are fed in parallel relationship through separate dies that are inserted into the open end empty of a container such as plastic laminate body tube having a dispensing nozzle and closure cap secured at one end, the tube being placed in an inverted vertical position with the open end up in sockets on a turntable or like conveyor which is indexed step by step through product filling and tube body closing stations. The extrusion of the separate dentifrice component layers is adjusted so that the two layers as they are jointly extruded in interfacial parallel relationship into the open end of the tube are in minimal interfacial surface contact as they enter the tube. After the filling of the tube with the multilayer product the open end of the tube is sealed. The dentifrice component layers are maintained in parallel, side-by-side interfacial surface layer contact in a multilayered configuration during storage. When maintained in this manner there is substantially no diffusion, bleeding or intermixing of the layers and the two component dentifrice product remains stable during storage in the tube.

The following examples illustrate this invention further. All proportions and amounts therein and elsewhere in this specification are by weight unless otherwise indicated.

EXAMPLE I

Anhydrous dentifrice compositions designated "Component 1" and "Component 2" were prepared having ingredients as set forth in Table I below.

TABLE I

Dentifrice Component Composition

| Ingredients | Component 1 wt % | Component 2 wt % |
|---|---|---|
| Glycerin | 19.75 | 20.25 |
| PEG 2000 | 3.00 | 3.00 |
| PEG 400 | 30.25 | 36.09 |
| Na Saccharin | 0.50 | 0.50 |
| FD&C - Blue #1 (1% soln) | — | 0.25 |
| FD&C - Yellow #10 (1% soln) | — | 0.25 |
| MFP | 0.80 | 0.76 |
| TSPP | 2.00 | 2.00 |
| STPP | 3.00 | 3.00 |
| $TiO_2$ | 2.00 | — |
| Zeodent 115 | 18.50 | 16.20 |
| Sylodent 15 | 3.00 | 3.00 |
| $NaHCO_3$ | 12.00 | 12.00 |
| $Na_2CO_3$ | 2.00 | 2.00 |

TABLE I-continued

Dentifrice Component Composition

| Ingredients | Component 1 wt % | Component 2 wt % |
|---|---|---|
| $CaO_2$ | 1.00 | — |
| Flavor | 1.00 | 1.00 |
| SLS | 1.70 | 1.70 |
| TOTAL | 100.00 | 100.00 |

To prepare Component 1, the glycerin, polyethylene glycol and sodium saccharin ingredients were dispersed in a conventional mixer until the mixture became a slurry, which was smooth in appearance, producing a homogeneous gel phase in which the MFP, TSPP, STPP and $TiO_2$ were added by mixing to prepare a despersion. The dispersion was transferred to a vacuum mixer, and the siliceous agents, sodium bicarbonate, sodium carbonate, calcium peroxide and flavor were then added and mixed for 10 to 30 minutes at high speed under a vacuum of about 50 mm Hg, to obtain a homogeneous mixture. The resultant product was a paste with satisfactory flavor and was white in color having a viscosity of $29 \times 10^6$ cps when measured 72 hours after preparation.

Component 2 was prepared in the same manner as that for Component 1 except the dyes Blue #1 and Yellow #1 were substituted for the $TiO_2$ pigment and calcium peroxide was removed. The resultant product was a gel with satisfactory flavor and was blue in color and had a viscosity of $29 \times 10^6$ cps when measured 72 hours after preparation.

A two layer dentifrice composition was prepared by feeding Component 1 and Component 2 through separate dies inserted into an empty plastic laminate body toothpaste tube having a dispensing nozzle and a closure cap secured at one end, the tube having been placed in an inverted vertical position with the open end up in sockets on a turntable which was indexed step by step through product filling tube body closing stations. The extrusion of the separate toothpaste layers was adjusted so that the layers of Component 1 and 2 as they were cojointly extruded into the open end of the tube formed a bilayer structure in which adjoining surfaces thereof were in interfacial contact as they entered the tube. After the filling of the tube with the bilayer components, the open end of the tube was sealed. The composite product was maintained in side-by-side surface layer contact in a bilayered configuration during storage.

When maintained in this manner no bleeding or intermixing of the layers was observed and the two component product remained stable without gas evolution during storage in the tube for at least 2 months at ambient temperature.

When the bilayered dentifrice of Example I was extruded from the toothpaste tube onto the bristles of a toothbrush, the two portions remained in interfacial contact and Component 2 appeared as a blue gel stripe on the surface of Component 1 which was opaque white whereby the extruded dentifrice had a blue striped appearance. No colorant fading was observed. The extruded toothpaste was sufficiently stable so that it did not distort and retained its extruded form while resting on the toothbrush bristles. Contact between the portions become intimate when the bilayer extrudate was intermixed during brushing of the teeth and gums with effective tooth polishing occurring with such intermixed contact.

By way of contrast, when 1% $CaO_2$ was included in Component 2, tubed samples of Component 2 which were initially green in color turned very slightly yellowish green in color when aged at 105° F. for 12 days and yellow in color when aged at 120° F. for 12 days.

To determine the effect on aging at elevated temperatures on the bilayer dentifrice of Example I, samples of the bilayer toothpaste packed in collapsible laminate tubes were exposed to heated air at 105° F. for a period of 12 weeks. No gasing of the tubes on test was noted indicating that the dentifrice composition was sufficiently stable for commercial use.

EXAMPLE II

Non-anhydrous dentifrice compositions having water incorporated therein designated "Component 3" and "Component 4" were prepared following the procedure of Example I having the ingredients set forth in Table II below:

TABLE II

Dentifrice Component Composition

| Ingredients | Component 3 wt % | Component 4 wt % |
|---|---|---|
| Glycerin | 25.00 | 25.00 |
| Propylene Glycol | 17.64 | 17.64 |
| PEG 600 | 3.00 | 3.00 |
| Na Saccharin | 0.50 | 0.50 |
| FD&C - Blue #1 (1 % soln) | — | 0.25 |
| FD&C - Yellow #10 (1 % soln) | — | 0.25 |
| MFP | 0.76 | 0.76 |
| TSPP | 2.00 | 2.00 |
| STPP | 3.00 | 3.00 |
| TiO$_2$ | 2.00 | — |
| Sodium Carboxymethyl Cellulose | 0.20 | 0.20 |
| Xantham Gum | 0.20 | 0.20 |
| Zeodent 115 | 21.00 | 22.99 |
| Sylodent 15 | 2.00 | 2.00 |
| Deionized Water | 6.00 | 5.51 |
| NaHCO$_3$ | 12.00 | 12.00 |
| Na$_2$CO$_3$ | 2.00 | 2.00 |
| CaO$_2$ | 1.00 | — |
| Flavor | 1.00 | 1.00 |
| SLS | 1.70 | 1.70 |
| TOTAL | 100.00 | 100.00 |

Component 3 had a viscosity of 35×10$^6$ cps and Component 4 had a viscosity of 37×10$^6$ cps when measured 72 hours after preparation.

To determine the effect on aging at elevated temperatures on the bilayer dentifrice of Example II, samples of the bilayer toothpaste packed in collapsible laminate tubes at 105° F. were exposed to heated air at 105° F. for 4 week and 2 month periods. No gasing of the tubes on test were noted indicating that the dentifrice was sufficiently stable for commercial use.

EXAMPLE III

To demonstrate the effect of the presence of an alkali metal compound on the gas stability in the composition of the present invention, the aging test procedure of Example I was repeated using dentifrice components designated "Compositions A and B" which contained 2% Na$_2$CO$_3$ or 2% K$_2$CO$_3$. The ingredients used to prepare Compositions A and B are listed in Table IV below. The aging test results are recorded in Table V below.

For purposes of comparison, the aging test was repeated except that the comparative dentifrice did not contain either Na$_2$CO$_3$ or K$_2$CO$_3$ but instead contained 2% by weight concentrations of MgCO$_3$ and CaCO$_3$. These comparative dentifrice components were designated Compositions C, D and E. The ingredients used to prepare the comparative compositions are also listed in Table IV and the aging test results for the comparative compositions are recorded in Tables V and VI.

TABLE IV

| Ingredients | A | B | C | D | E |
|---|---|---|---|---|---|
| Glycerin | 20.25 | 20.25 | 20.25 | 20.25 | 20.25 |
| PEG 400 | 30.79 | 30.79 | 30.79 | 30.79 | 30.79 |
| Na Saccharin | 0.50 | 0.50 | 0.50 | 0.50 | 0.50 |
| MFP | 0.76 | 0.76 | 0.76 | 0.76 | 0.76 |
| TSPP | 2.00 | 2.00 | 2.00 | 2.00 | 2.00 |
| NaTPP | 3.00 | 3.50 | 3.50 | 3.00 | 3.50 |
| TiO$_2$ | 2.00 | 2.00 | 2.00 | 2.00 | 2.00 |
| ZEO 115 | 18.00 | 18.00 | 20.00 | 18.00 | 18.00 |
| Sylodent 15 | 4.00 | 4.00 | 4.00 | 4.00 | 4.00 |
| Na Bicarbonate | 12.00 | 12.00 | 12.00 | 12.00 | 12.00 |
| Na Carbonate | 2.00 | — | — | — | — |
| K Carbonate | — | 2.00 | — | — | — |
| Ca Carbonate | — | — | — | 2.00 | — |
| Mg Carbonate | — | — | — | — | 2.00 |
| Ca Peroxide | 2.00 | 2.00 | 2.00 | 2.00 | 2.00 |
| Flavor | 1.00 | 1.00 | 1.00 | 1.00 | 1.00 |
| SLS | 1.70 | 1.70 | 1.70 | 1.70 | 1.70 |
| TOTAL | 100.00 | 100.00 | 100.00 | 100.00 | 100.00 |

TABLE V

Aging @ 105° F.
Composition

| TIME (Days) | A | B | C | D | E |
|---|---|---|---|---|---|
| 3 | OK* | OK | bloated, no bubbles | sl. bloated sl. airy | bloated v. airy |
| 7 | OK | OK | airy | bloated, airy | bloated, airy |

TABLE VI

Aging @ 120° F.
Composition

| TIME (Days) | A | B | C | D | E |
|---|---|---|---|---|---|
| 3 | OK* | OK | crimp failed bloated, sl. airy | sl. bloated | bloated v. airy |
| 7 | OK | OK | sl. airy | crimp failed, bloated airy | bloated, airy |

*OK means no bloating or bubbles observed in aged product.

The results recorded in Tables V and VI indicate that alkali metal compounds such as Na$_2$CO$_3$ and K$_2$CO$_3$ impart stability to bicarbonate containing dentifrice formulations in which reactive ingredients such as peroxide and bicarbonate are present whereas equivalent alkaline metal compounds do not impart any stability to the dentifrice formulation.

What is claimed is:

1. An extrudable composite multilayer dentifrice composition for cleaning teeth containing a calcium peroxide ingredient which does not react with other ingredients of the composition during storage or when extruded from a container onto a toothbrush, the composition comprising two substantially anhydrous dentifrice components, one component containing a calcium peroxide ingredient and colorant but free of any colorants reactive with calcium dentifrice components one component containing sodium bicarbonate and a colorant reactive with the peroxide ingredient, the components having substantially equivalent viscosity which are maintained in stable discrete layered phases in interfacial contact with each other prior to extrusion without interaction of the peroxide and the colorant ingredients and which are extrudable together in interfacial contact without interaction of the ingredients the colorants being of contrasting color to form a striped dentifrice when extruded.

2. The dentifrice composition of claim 1 wherein a pigment and a dye of contrasting color are separately included in the separate dentifrice components to form a striped dentifrice product upon extrusion.

3. A method of cleaning teeth which comprises preparing an extrudable composite multilayer dentifrice composition containing a peroxide ingredient which does not interact or react with other ingredients of the dentifrice during storage or when extruded together from a container onto a toothbrush, the composition comprising two substantially anhydrous dentifrice components, one component containing calcium peroxide and colorant but free of any colorants reactive with calcium peroxide and the other component containing sodium bicarbonate and a colorant reactive with the peroxide, the colorants being of contrasting color to form a striped dentifrice when extruded the components having substantially equivalent viscosity which are maintained in stable discrete layered phases in interfacial contact with each other prior to extrusion without interaction of the peroxide and colorant and colorant ingredients, extruding onto a brush the components together in interfacial contact without interaction of the ingredients and then mixing the components to clean teeth in the oral cavity.

4. The method of claim 3 wherein a pigment and a dye of contrasting colors are separately included in the separate dentifrice components.

* * * * *